(12) United States Patent
Tripathi

(10) Patent No.: US 10,398,598 B2
(45) Date of Patent: Sep. 3, 2019

(54) APPARATUS AND METHODS FOR PERFORMING ENHANCED VISUALLY DIRECTED PROCEDURES UNDER LOW AMBIENT LIGHT CONDITIONS

(71) Applicant: TrueVision Systems, Inc., Goleta, CA (US)

(72) Inventor: Ashok B. Tripathi, Santa Barbara, CA (US)

(73) Assignee: TrueVision Systems, Inc., Santa Barbara, CA (US)

( * ) Notice: Subject to any disclaimer, the term of this patent is extended or adjusted under 35 U.S.C. 154(b) by 806 days.

(21) Appl. No.: 14/923,132

(22) Filed: Oct. 26, 2015

(65) Prior Publication Data

US 2016/0038337 A1    Feb. 11, 2016

Related U.S. Application Data

(62) Division of application No. 12/417,115, filed on Apr. 2, 2009, now Pat. No. 9,168,173.
(Continued)

(51) Int. Cl.
*A61F 9/008* (2006.01)
*A61B 3/00* (2006.01)
(Continued)

(52) U.S. Cl.
CPC ............ *A61F 9/008* (2013.01); *A61B 3/0025* (2013.01); *A61B 3/0058* (2013.01);
(Continued)

(58) Field of Classification Search
CPC ..... A61B 3/145; A61B 3/0025; A61B 3/0058; A61B 3/1015
See application file for complete search history.

(56) References Cited

U.S. PATENT DOCUMENTS 3,431,992 A    3/1969  Whitecar
3,517,183 A    6/1970  Rebres
(Continued)

FOREIGN PATENT DOCUMENTS

DE    3431992    4/1985
JP    3209543    9/1991
(Continued)

OTHER PUBLICATIONS

US 3,973,836 A, 08/1976, Govignon et al. (withdrawn)
(Continued)

*Primary Examiner* — Bobbak Safaipour
(74) *Attorney, Agent, or Firm* — Quinn IP Law

(57) ABSTRACT

A system, method, and apparatus for performing enhanced visually directed procedures under low ambient light conditions are disclosed. An example method includes acquiring at least one real-time high resolution video signal representing at least one view of an eye in at least one wavelength of light outside of the wavelengths of visible light. The example method also includes converting the at least one view corresponding to the at least one real-time high resolution video signal at the at least one wavelength of light outside of the wavelengths of visible light into at least one wavelength of visible light. The at least one real-time high resolution video signal is acquired after light conditions are low enough such that a pupil of the eye does not constrict substantially from its maximum pupillary diameter.

20 Claims, 3 Drawing Sheets

Related U.S. Application Data

(60) Provisional application No. 61/042,606, filed on Apr. 4, 2008.

(51) Int. Cl.
*A61B 3/13* (2006.01)
*A61B 3/14* (2006.01)
*G02B 21/36* (2006.01)
*G02B 23/12* (2006.01)
*A61B 3/10* (2006.01)

(52) U.S. Cl.
CPC .............. *A61B 3/1015* (2013.01); *A61B 3/13* (2013.01); *A61B 3/145* (2013.01); *G02B 21/361* (2013.01); *G02B 23/12* (2013.01); *A61F 2009/00853* (2013.01)

(56) References Cited

U.S. PATENT DOCUMENTS

| | | |
|---|---|---|
| 3,867,697 A | 2/1975 | Vanzetti et al. |
| 4,395,731 A | 7/1983 | Schoolman |
| 4,691,997 A | 9/1987 | Munchel |
| 4,786,115 A | 11/1988 | Fantone et al. |
| 4,786,155 A | 11/1988 | Fantone et al. |
| 4,790,305 A | 12/1988 | Zoltan |
| 4,791,478 A | 12/1988 | Tredwell et al. |
| 4,967,268 A | 10/1990 | Lipton et al. |
| 4,989,078 A | 1/1991 | Paxton |
| 4,995,716 A | 2/1991 | Warnicki et al. |
| 5,007,715 A | 4/1991 | Verhulst |
| 5,022,744 A | 6/1991 | Leiter |
| 5,045,936 A | 9/1991 | Lobb et al. |
| 5,048,946 A | 9/1991 | Sklar et al. |
| 5,054,907 A | 10/1991 | Sklar et al. |
| 5,098,426 A | 3/1992 | Sklar et al. |
| 5,109,276 A | 4/1992 | Nudelman et al. |
| 5,193,000 A | 3/1993 | Lipton et al. |
| 5,200,838 A | 4/1993 | Nudelman et al. |
| 5,513,005 A | 4/1996 | Muller et al. |
| 5,530,494 A | 6/1996 | Ogawa et al. |
| 5,545,120 A | 8/1996 | Chen et al. |
| 5,548,355 A | 8/1996 | Iki |
| 5,568,188 A | 10/1996 | Widmer et al. |
| 5,579,772 A | 12/1996 | Kinikawa et al. |
| 5,652,676 A | 7/1997 | Grinblat |
| 5,694,198 A * | 12/1997 | Ueno .................. A61B 3/103 351/208 |
| 5,715,836 A | 2/1998 | Kliegis et al. |
| 5,740,802 A | 4/1998 | Nafis et al. |
| 5,751,927 A | 5/1998 | Wason |
| 5,815,240 A | 9/1998 | Iki |
| 5,825,532 A | 10/1998 | Mochizuki et al. |
| 5,835,133 A | 11/1998 | Moreton et al. |
| 5,867,210 A | 2/1999 | Rod |
| 5,867,309 A | 2/1999 | Spink et al. |
| 5,870,137 A | 2/1999 | Stuettler |
| 5,873,822 A | 2/1999 | Ferre et al. |
| 5,912,763 A | 6/1999 | Spink |
| 5,933,513 A | 8/1999 | Yoneyama et al. |
| 5,999,840 A | 12/1999 | Grimson et al. |
| 6,006,126 A | 12/1999 | Cosman |
| 6,069,733 A | 5/2000 | Spink et al. |
| 6,088,470 A | 7/2000 | Camus et al. |
| 6,133,762 A | 10/2000 | Hill et al. |
| 6,133,945 A | 10/2000 | Stuettler |
| 6,144,762 A | 11/2000 | Brooks |
| 6,147,797 A | 11/2000 | Lee |
| 6,179,421 B1 | 1/2001 | Pang |
| 6,191,809 B1 | 2/2001 | Hori et al. |
| 6,201,894 B1 | 3/2001 | Funda et al. |
| 6,201,984 B1 | 3/2001 | Funda et al. |
| 6,241,672 B1 | 6/2001 | Hochman et al. |
| 6,256,529 B1 | 7/2001 | Holupka et al. |
| 6,276,799 B1 | 8/2001 | Van Sarloos et al. |
| 6,318,860 B1 | 11/2001 | Yoshikatsu |
| 6,337,765 B1 | 1/2002 | Spink et al. |
| 6,396,627 B1 | 5/2002 | Tachihara et al. |
| 6,441,958 B1 | 8/2002 | Yeung et al. |
| 6,483,948 B1 | 11/2002 | Spink et al. |
| 6,522,906 B1 | 2/2003 | Salisbury, Jr. et al. |
| 6,596,025 B2 | 7/2003 | Portney |
| 6,607,527 B1 | 8/2003 | Ruiz |
| 6,631,990 B2 | 10/2003 | Schippert |
| RE38,307 E | 11/2003 | Gustafsson et al. |
| 6,643,070 B2 | 11/2003 | Deverin et al. |
| 6,675,032 B2 | 1/2004 | Chen et al. |
| 6,685,317 B2 | 2/2004 | Su et al. |
| 6,697,664 B2 | 2/2004 | Kienzle, III et al. |
| 6,765,718 B1 | 7/2004 | Spink et al. |
| 7,025,459 B2 | 4/2006 | Cornsweet et al. |
| 7,066,928 B2 | 6/2006 | Dick |
| 7,110,614 B2 | 9/2006 | Launay et al. |
| 7,146,983 B1 | 12/2006 | Hohla |
| 7,261,415 B2 | 8/2007 | Chernyak et al. |
| 7,313,430 B2 | 12/2007 | Urquhart et al. |
| 7,320,685 B2 | 1/2008 | Feige et al. |
| 7,331,667 B2 | 2/2008 | Grotehusmann et al. |
| 7,370,965 B2 | 5/2008 | Kojima |
| 7,428,001 B2 | 9/2008 | Schowengerdt et al. |
| 7,431,457 B2 | 10/2008 | Chernyak |
| 7,654,668 B2 | 2/2010 | Neuhann et al. |
| 7,695,136 B2 | 4/2010 | Dai |
| 7,831,096 B2 | 11/2010 | Williamson, Jr. |
| 7,905,887 B2 | 3/2011 | Moeller et al. |
| 7,959,289 B2 | 6/2011 | Cattin-Liebl |
| 8,025,400 B2 | 9/2011 | Chernyak |
| 8,057,038 B2 | 11/2011 | Dai et al. |
| 8,088,124 B2 | 1/2012 | Loesel et al. |
| 8,131,343 B2 | 3/2012 | Burgkart |
| 8,186,830 B2 | 5/2012 | Grotehusmann et al. |
| 8,192,445 B2 | 6/2012 | Parmer et al. |
| 8,375,956 B2 | 2/2013 | Gray et al. |
| 8,414,123 B2 | 4/2013 | Boukhny et al. |
| 8,454,160 B2 | 6/2013 | Dai |
| 8,474,974 B2 | 7/2013 | Dai |
| 8,486,085 B2 | 7/2013 | Moeller et al. |
| 8,528,566 B2 | 9/2013 | Loesel et al. |
| 8,708,488 B2 | 4/2014 | Kraus |
| 8,740,385 B2 | 6/2014 | Chernyak |
| 8,784,443 B2 | 7/2014 | Tripathi |
| 8,848,869 B2 | 9/2014 | Gertner et al. |
| 8,978,660 B2 | 3/2015 | Chernyak et al. |
| 9,168,173 B2* | 10/2015 | Tripathi .................. A61B 3/13 |
| 9,173,717 B2* | 11/2015 | Tripathi .................. A61F 2/16 |
| 2002/0063850 A1 | 5/2002 | Barry et al. |
| 2002/0080478 A1 | 6/2002 | Mannss |
| 2002/0087149 A1* | 7/2002 | McCary .................. A61B 90/36 606/4 |
| 2002/0097378 A1 | 7/2002 | Saito et al. |
| 2002/0156345 A1 | 10/2002 | Eppler |
| 2003/0021016 A1 | 1/2003 | Grier |
| 2003/0053025 A1 | 3/2003 | Turner et al. |
| 2003/0055410 A1 | 3/2003 | Evans et al. |
| 2003/0071893 A1 | 4/2003 | Miller et al. |
| 2003/0120266 A1 | 6/2003 | Fujieda |
| 2003/0142271 A1 | 7/2003 | Ross et al. |
| 2003/0184855 A1 | 10/2003 | Yasuda et al. |
| 2003/0185450 A1 | 10/2003 | Garakani et al. |
| 2003/0223037 A1 | 12/2003 | Chernyak |
| 2004/0017607 A1 | 1/2004 | Hauger et al. |
| 2004/0227828 A1 | 11/2004 | Loose |
| 2004/0252276 A1 | 12/2004 | Nanjo et al. |
| 2004/0263785 A1 | 12/2004 | Chernyak |
| 2004/0264765 A1 | 12/2004 | Ohba |
| 2005/0007659 A1 | 1/2005 | Steinthal et al. |
| 2005/0014996 A1 | 1/2005 | Konomura et al. |
| 2005/0018135 A1 | 1/2005 | Maeda et al. |
| 2005/0024720 A1 | 2/2005 | Cartlidge et al. |
| 2005/0025365 A1 | 2/2005 | Oosawa |
| 2005/0046930 A1 | 3/2005 | Olschewski |
| 2005/0071087 A1 | 3/2005 | Anderson |
| 2005/0107808 A1 | 5/2005 | Evans et al. |
| 2005/0111088 A1 | 5/2005 | Winterot et al. |

(56) References Cited

U.S. PATENT DOCUMENTS

| | | | |
|---|---|---|---|
| 2005/0117118 A1 | 6/2005 | Miller et al. | |
| 2005/0128573 A1 | 6/2005 | Merz | |
| 2005/0200808 A1 | 9/2005 | Wyatt | |
| 2005/0203384 A1 | 9/2005 | Sati et al. | |
| 2005/0225721 A1 | 10/2005 | Harris et al. | |
| 2006/0084955 A1* | 4/2006 | Hindi | A61F 9/008 606/12 |
| 2006/0116668 A1 | 6/2006 | Gray et al. | |
| 2006/0223037 A1 | 10/2006 | Tanda | |
| 2007/0121202 A1 | 5/2007 | Riederer | |
| 2007/0121203 A1 | 5/2007 | Riederer | |
| 2007/0188603 A1 | 8/2007 | Riederer et al. | |
| 2008/0100801 A1* | 5/2008 | Yahagi | A61B 3/0033 351/206 |
| 2008/0103367 A1 | 5/2008 | Burba et al. | |
| 2008/0118115 A1 | 5/2008 | Williamson | |
| 2008/0139082 A1* | 6/2008 | Schnuckle | A63H 3/38 446/392 |
| 2008/0247616 A1 | 10/2008 | Pescatore et al. | |
| 2009/0033867 A1* | 2/2009 | Dai | A61F 9/00806 351/205 |
| 2009/0048608 A1 | 2/2009 | Boukhny et al. | |
| 2009/0079936 A1* | 3/2009 | Robert | A61B 3/1173 351/206 |
| 2009/0125088 A1 | 5/2009 | Schleicher et al. | |
| 2009/0137988 A1 | 5/2009 | Kurtz | |
| 2009/0143772 A1 | 6/2009 | Kurtz | |
| 2009/0171358 A1 | 7/2009 | Chang et al. | |
| 2009/0236541 A1* | 9/2009 | Lomnes | A61B 1/043 250/458.1 |
| 2009/0254070 A1 | 10/2009 | Tripathi | |
| 2010/0045933 A1 | 2/2010 | Eberl et al. | |
| 2010/0094262 A1 | 4/2010 | Tripathi | |
| 2010/0208199 A1 | 8/2010 | Levis et al. | |
| 2010/0217278 A1 | 8/2010 | Tripathi | |
| 2011/0064286 A1 | 3/2011 | Chien et al. | |
| 2011/0092984 A1 | 4/2011 | Tripathi | |
| 2011/0102549 A1 | 5/2011 | Takahashi | |
| 2011/0160578 A1 | 6/2011 | Tripathi | |
| 2011/0202046 A1 | 8/2011 | Angeley et al. | |
| 2011/0213342 A1 | 9/2011 | Tripathi | |
| 2011/0224657 A1 | 9/2011 | Stevens et al. | |
| 2011/0249311 A1* | 10/2011 | Engelhardt | G02B 21/0048 359/201.2 |
| 2011/0274322 A1 | 11/2011 | Kern et al. | |
| 2011/0286630 A1 | 11/2011 | Harder et al. | |
| 2012/0172854 A1 | 7/2012 | Raymond et al. | |
| 2012/0242956 A1 | 9/2012 | Chernyak | |
| 2014/0114297 A1 | 4/2014 | Woodley et al. | |
| 2014/0125949 A1 | 5/2014 | Shea et al. | |
| 2014/0257258 A1 | 9/2014 | Kurtz | |
| 2014/0303486 A1 | 10/2014 | Baumgartner et al. | |
| 2014/0316388 A1 | 10/2014 | Hipsley | |
| 2014/0324071 A1 | 10/2014 | Tripathi | |
| 2015/0221105 A1 | 8/2015 | Tripathi et al. | |
| 2016/0051360 A1 | 2/2016 | Tripathi | |
| 2016/0113727 A1 | 4/2016 | Tripathi et al. | |

FOREIGN PATENT DOCUMENTS

| | | |
|---|---|---|
| JP | 2009-061035 | 3/2009 |
| WO | 2000/060992 | 10/2000 |
| WO | 2000/060998 | 10/2000 |
| WO | 2003/030763 | 4/2003 |
| WO | 2005/000139 A1 | 1/2005 |
| WO | 2005/042760 | 5/2005 |
| WO | 2009/158517 A3 | 12/2009 |

OTHER PUBLICATIONS

International Search Report for PCT/US2011/025746.

International Search Report for PCT/US2013/057686 dated Mar. 6, 2014.

John Chang, M.D., Cyclotorsion during laser in situ keratomileusis, J. Cataract Refract Surg, 34:1720-1726 (2008).

Suenaga et al., Real-time in situ three-dimensional integral videography and surgical navigation using augmented reality: a pilot study. International Journal of Oral Science 5: 98-102 (2013).

TrueVision Systems Inc., 510K Application Summary for TrueVision 3D Visualization and Guidance System, Dec. 22, 2010.

U.S. Office Action dated Mar. 29, 2016 for U.S. Appl. No. 13/024,948, filed Feb. 10, 2011.

U.S. Office Action dated May 12, 2016 for U.S. Appl. No. 14/424,985, filed Feb. 27, 2015.

Gering et al., An integrated visualization system for surgical planning and guidance using image fusion and interventional imaging. Medical Image Computing and Computer Assisted Intervention—Miccai '99. Second International Conference, Cambridge, UK, Sep. 19-22, 1999, pp. 809-819.

Supplementary European Search Report for European Patent Application 13834045 dated Jul. 14, 2017.

Rupert Menapace, MD, Posterior Capsulorrhexis and Optic Buttoning—In Combined with Anterior Capsule Polishing, Cataract & Refractive Surgery Today Europe, Jan./Feb. 2008, pp. 16-19.

Edward J. Holland, MD, Acrysof Toric IOL: Surgical Pearls, Cataract & Refractive Surgery Today, May 2006, pp. 71-72

Ron Rajecki, The future of cataract surgery: Improved ergonomics, Ophthalmology Times, Jul. 1, 2009.

Stephen Nellis, Venture capital in a freeze—But Santa Barbara med-tech company isn't giving up, Pacific Coast Business Times, Jan. 25, 2009.

James P. Gills, MD, Nomogram for Limbal Relaxing Incisions with Cataract Surgery.

Canrobert Oliveira, MD, The 'Keratopyramis Phenomenum' and The Canrobert 'C' Procedure, International Society of Refractive Keratoplasty 193 Pre-American Academy of Ophthalmology, Nov. 12, 1993 and Nov. 13, 1993 Chicago, Illinois USA.

Louis D. "Skip" Nichamin, MD, Management of Astigmatism at the Time of Lens-Based Surgery, Tasman W. Jaeger E.A., Duane's Clinical Ophthalmology, 2006 Edition.

Robert J. Weinstock, MD, Heads Up Cataract Surgery Using the Truevision 3D System.

Posted by RCJones, Bascom Palmer Eye Institute again ranked nation's No. 1 eye hospital by U.S. News & World Report, Jul. 17, 2009, <URL: http://everitas.univmiami.net/2009/07/17/bascom-palmer-eye-institute-again-ranked-nations-no-1-eye-hospital-by-us-news-world-report/.

"Eye Surgery Using 3D Technology," WSFL video clip, <URL: http://southflorida.sun-sentinel.com/videobeta/watch/?watch=d69be520-0d51-4a4d-b2d2-d27f20f4bfcc&cat=empty&src=front&title=Eye%20surgery%20using%203D%20technology/.

Technology to perform LRIs using lasers [online]. OptiMedica [retrieved on Oct. 20, 2009]. retrieved from the Internet, <URL:http://www.optimedica.com/.

Technology to perform LRIs using lasers [online]. LenSx Lasers, Inc. [retrieved on Oct. 20, 2009]. retrieved from the Internet, <URL:http://www.ventureinvestors.com/archives/1516.

Technology to perform LRIs using lasers [online]. LensAR Inc. [retrieved on Oct. 20, 2009]. retrieved from the Internet, <URL:http://www.sujanani.com/lasik/lasik_surgery/?p=101859.

Retrieved on Aug. 27, 2008. retrieved from the Internet, <URL:http://www.LRIcalculator.com.

DentiMag3D. Product Description [online]. StereoImaging Corporation [retrieved on Oct. 13, 2005]. retrieved from the Internet: <URL:http://www.stereoimaging.com/products/dentimag.html>.

Leica IC 3D. product Description [online]. Leica Microsystems [retrieved on Oct. 13, 2005]. Retrieved from the Internet: <URL: http://www.oleica-microsystems.com/website/lms.nsf?opendatabase &path4website/products.nsf/(ALLIDs)/ECFFFC6CF17470FEC125706D002FBF06>.

The World's Only: Interactive Leica 3D System for Microscopy. Press Release [online]. Leica Microsystems, Jun. 24, 2005, pp. 1-2 [retrieved on Oct. 13, 2005]. Retrieved from the Internet: <URL:http://www.leica-microsystems.com/website/lms.nsf?opendatabase&path=/website/products.nsf/(ALLIDs)/ECFFFcC F17470FEC125706D002FBF06>.

(56) References Cited

OTHER PUBLICATIONS

Leica ICD: compact, Integrated Digital Camera for stereomiroscopes. Brochure [online]. Leica Microsystems, 2005, pp. 1-4 [retrieved on Apr. 20, 2006]. Retrieved from the Internet:<URL:http://www.leica-microsystems.com/website/lms.nsf?opendatabase&path=WebSite/Download.nsf/(ALLIDs)/1C611440E77FF0EFC125700B003E478C>.

* cited by examiner

APPARATUS AND METHODS FOR PERFORMING ENHANCED VISUALLY DIRECTED PROCEDURES UNDER LOW AMBIENT LIGHT CONDITIONS

PRIORITY CLAIM

This application claims priority to and the benefit as a divisional application of U.S. patent application Ser. No. 12/417,115, filed Apr. 2, 2009, entitled, "Apparatus and Methods for Performing Enhanced Visually Directed Procedures Under Low Ambient Light Conditions", which claims priority to and the benefit of U.S. Provisional Application No. 61/042,606, filed on Apr. 4, 2008, the entire contents of which are herein incorporated by reference.

TECHNICAL FIELD

The present disclosure generally relates to apparatus and associated methods for performing enhanced visually directed procedures under low ambient light conditions on target objects including surgical procedures on structures and tissues within the body, particularly procedures related to the measurement and treatment of ocular conditions.

BACKGROUND

Throughout history it has been axiomatic to those of ordinary skill in the art that in order to perform delicate or meticulous processes and procedures with enhanced levels of control and with improved performance and outcomes the operators, technicians, surgeons, or other performers of the procedures must have good visual control of the various steps and details of the respective processes. Typically, the best way to improve visual control of a process is to increase the amount of visible light available in the workspace to brightly illuminate the target object or working area with shadow-free white light. One need only look at the high wattage lighting of a contemporary precision assembly line or at the bright lights of an operating room or dentist's office to appreciate how important good lighting is to the precise visual control and to the successful outcome of a delicate or precision procedure.

More recently, magnification and microscopy have been incorporated into meticulous testing and assembly processes and into similarly meticulous operating theater procedures to further improve the ability of the process operators to see what they are working on and to allow them to better visually control each step of the process. For example, ocular surgical procedures are now commonly performed under stereomicroscopes that enable the ocular surgeons to view the minute details and responses of various tissues within a patient's eye to the delicate steps of the procedures involved. In addition to the bright ambient room lighting of the operating room or surgical theater, stereomicroscopes can include their own internal sources of visible light to further illuminate the target tissues under the microscopic control of the operating surgeon.

Even more recently, electronic imaging has been incorporated into various processing and medical techniques to free the operators and surgeons from the awkward tedium of peering into the fixed eyepieces of conventional stereomicroscopes. Digital signal processing of such electronic images can provide an additional degree of visual acuity that can facilitate the performance of a meticulous process such as eye surgery. The present inventors recently provided a three dimensional high definition visual display platform that can take the images from a conventional stereomicroscope and present them to an operator or surgeon on a conveniently located screen. Moreover, the digital three dimensional images can be electronically processed to increase magnification or to improve signal quality and content.

However, there are circumstances where bright visible lighting can actually be detrimental to the performance of a meticulous process. For example, bright visible lighting can have negative effects which an operator such as a surgeon must endure. Hot operating room lighting can cause discomfort to a surgeon as well as to the patient. In some circumstances visors may need to be worn to reduce glare from the bright lights that must be in close proximity to the process target on an assembly line. Bright visible lighting also can take up room and floor space within an assembly line or operating theatre, further complicating the processes being performed. Reducing the lighting to improve operator comfort reduces the ability of the operators to see and visually control the processes.

Additionally, there are processes and procedures where bright visible lighting itself is detrimental to the outcome of the process. A photographic darkroom is an example of an environment where bright lighting, however useful to operator control, can be disastrous to the outcome of the process. Similar problems have been reported in ocular surgery such as cataract removal where bright lights of varying colors and wavelengths utilized in the surgeries have been found to be detrimental to the response of retinal tissue within the eye and may even have toxic effects on eye tissues.

Similarly, many types of modern eye surgery utilize lasers or other instruments to fuse or excise ocular tissues in order to correct medical conditions through processes such as fusing detached retinas to underlying tissues, sealing leaking retinal vasculature, removing opaque posterior capsule tissues from in front of the retina, or resculpting the shape and optical performance of a patient's cornea to correct distorted vision. To best accomplish these and other procedures the ocular surgeon would prefer to have the greatest possible visualization and resultant control of the meticulous process. However, bright ambient lighting or bright microscope lighting has exactly the opposite result because the patient's pupil constricts as a natural response to bright visible light and restricts or eliminates access to the target ocular tissues within the eye. Thus, prior to the present invention, an ocular surgeon had to sacrifice open pupillary access to internal eye tissues in exchange for illuminating those tissues with sufficient light to make them visible to operate on.

An acute example of a circumstance where bright visible lighting is actually a potential limitation to a successful result is the vision correction procedure known as laser-assisted in situ keratomileusis or "LASIK". In LASIK a surgeon first measures the optical properties of a patient's eye to determine the amount and type of correction necessary to improve vision. This is best accomplished when the patient's pupil is completely dilated to its natural extent so that the greatest area of the patient's cornea can be measured for subsequent laser sculpting. Bright visible lighting interferes with this objective by causing the patient's pupil to constrict from its natural maximum dark or night vision diameter of approximately 8 millimeters to 1.5 millimeters or less, significantly limiting the area of the patient's cornea that can be measured and subsequently resculpted.

Though it is possible to dilate a patient's pupil with pharmaceutical compounds such as tropicamide, pharmaceutical dilation often results in an unnatural pupilliary diameter that can be distorted or off center. This further complicates the ocular measurement process by introducing another variable to the performing surgeon, potentially limiting control and impacting the outcome of the process. Additionally, tropicamide achieves dilation by temporarily paralyzing the muscles responsible for focusing in the patient's eye. This paralysis usually lasts at least a few hours and therefore the patient cannot safely operate a motorized vehicle to return home until the paralyzing effects of the chemical dilators have completely subsided or been chemically reversed by compounds such as dapiprazole.

Though it is possible to measure the optical functioning of a patient's eye in subdued light conditions in an effort to expand pupillary dilation without chemicals, it is not possible to perform the subsequent surgical sculpting procedure on the patient's cornea in the absence of visible light without sacrificing control. As a result, there is a significant need in the art for methods and apparatus that will enhance the outcome of such delicate or meticulous visually directed procedures.

SUMMARY

These and other objects are achieved by the apparatus and methods of the present invention which, in a broad aspect, provide novel visualization platforms for performing enhanced visually directed procedures on target objects or tissues under low ambient lighting conditions. The visualization platforms of the present invention can be stand-alone apparatus or retro-fit to existing optical systems such as stereomicroscopes. In a broad aspect the visualization platforms include at least one high resolution photosensor which is capable of receiving and acquiring a plurality of optical views of the target object of the process in at least one wavelength outside of the wavelengths of normal visible light. The high resolution photosensor then transmits a resultant real-time high resolution video signal which is received by at least one high resolution video display that, because of the multiple high resolution optical views presented, can be viewed by the operator or others as a real-time high definition three dimensional visual image in spite of the absence of substantial amounts of ambient or direct visible light. These real-time high definition three dimensional visual images include minute visual details as well as the real-time responses of the target objects and tissues involved to the various steps of the processes even though the presence of visible light is markedly reduced or even essentially eliminated.

This significantly improves the comfort and stamina of the process operator or surgeon as well as the comfort and compliance of a surgical patient while providing the operator or surgeon with enhanced visual control of the process. Reduced or low ambient lighting in the visible wavelengths makes the operating environment more comfortable by reducing the heat associated with high output lighting. Removing the need for such lighting also frees up valuable process or operating room space that used to be devoted to lighting fixtures.

Of equal importance, reducing ambient visible lighting functions to reduce or remove phototoxicity and dyschromatopsia in surgical patients. Reduced ambient visible light also reduces reflected glare and high contrast shadows that can confuse or overwhelm the vision of the operator or surgeon, particularly when the operator or surgeon shifts his focus away from the target object and back again. In the past, the operator or surgeon would have to pause in order to allow his own eyes to adjust to the changes in lighting when he shifted his focus away from the microscope to the surrounding environment in order to adjust equipment or change tools. The present invention eliminates these pauses and delays while it facilitates the operator's or surgeon's ability to view the surrounding environment while maintaining acute visual control of the target process.

"Visible light" is commonly understood to be light having wavelengths corresponding to the visible or optical spectrum. Normally perceived as white in color, when refracted or bent through an optical prism visible light spreads out into differing wavelengths corresponding to the characteristic colors of the rainbow. Scientifically speaking, visible light is that portion of the electromagnetic spectrum having a wavelength of about 380 nanometers (1 nanometer=$1 \times 10^{-9}$ m) to about 750 nanometers where the normal human eye will respond to the electromagnetic energy and perceive the presence of light. In terms of frequency, visible light corresponds to a frequency band in the vicinity of 400-790 terahertz. A light-adapted eye generally has its maximum sensitivity at around 555 nm (540 THz), in the green region at the middle of the optical spectrum. The present visualization platform has at least one high resolution photosensor which can detect at least one wavelength or frequency of light outside of this range.

Exemplary wavelengths within the scope and teachings of the present invention that are outside of the wavelengths of normal visible light can be longer or shorter than the visible light wavelengths and include at least one longer wavelength of light that is between about 700 nanometers and about 1400 nanometers and at least one wavelength of light that is shorter than about 400 nanometers. As those skilled in the art will appreciate, such longer wavelengths are commonly referred to as infrared or "IR" wavelengths, and are not visible to the eye; whereas shorter wavelengths are commonly referred to as ultraviolet or "UV" wavelengths.

Utilizing the teachings of the present invention the operator or surgeon can inspect or measure a target object or tissue under light conditions having visible light present in amounts that are insufficient to cause heating or discomfort to the operator, surgeon, or patient, or damage to the target object or tissue without sacrificing visual acuity or control. Then, the operator or surgeon can perform a subsequent procedure on the target object or tissue under light conditions that are substantially identical to the light conditions of the inspecting step. In this manner, the present invention improves the comfort and control of the process operator or surgeon and directly enhances the outcome of the process by removing visual distractions, discomfort, and fatigue.

Target objects or tissues which are contemplated as being within the scope of the present invention include anything for which visualization with wavelengths of light outside of the wavelengths of visible light would be beneficial. These may include, without limitation, microelectronics and micromechanical articles and devices or other precision devices such as watches and the like. They also may include, without limitation, tissues within the human body such as the eyes, ears, nose, and throat, the brain, heart, vasculature, joints, tumors, or any other part of the human body.

An exemplary embodiment of the apparatus and methods of the present invention that is particularly well suited to illustrate its features and advantages is a visually directed procedure on an eye such as laser surgery exemplified by LASIK corneal resculpting. Utilizing the teachings of the present invention a LASIK surgeon first inspects the patient's eye under light conditions having insufficient visible light to cause the patient's pupil to constrict substantially from its maximum pupillary diameter. Then the LASIK surgeon performs the corneal resculpting under substantially identical lighting conditions.

As those skilled in the art will appreciate, during the enhanced LASIK procedure of the present invention, because the patient's eye does not have to react to relatively bright visible light the patient's pupil remains dilated at or near its normal or natural maximum pupillary diameter. This enables the ocular surgeon performing the procedure to achieve an enhanced outcome including improved overall corrections and improved night vision because a more accurate and complete diagnostic waveform can be measured for the target eye with a completely dilated natural pupillary diameter.

Further, because the subsequent sculpting procedure is performed under substantially identical low visible light conditions to the initial inspecting or measuring step, the LASIK surgeon can better align and adjust the LASIK apparatus to an essentially identical and therefore familiar target while the apparatus and associated methods of the present invention provide the surgeon with a real-time, high resolution three dimensional video image of the target object or tissue derived from the non-visible wavelengths which provides the surgeon with precise control over the procedure.

Of equal importance, the patient is less likely to move or change position in response to bright lights because the procedures of the present invention are performed without bright visible lighting shining directly into the patient's eye. This has the added benefit of making the patient both more comfortable and more stably compliant, further enhancing the procedure and its outcome by virtually eliminating subtle twitching and movement in response to the discomfort of bright ambient lighting. Similarly, the elimination of hot visible light lamps which may require a surgeon to wear visors to reduce glare enhances the comfort and stamina of the LASIK surgeon during the procedure. Thus, when utilizing the apparatus and methods of the present invention, an operator or surgeon may perform the enhanced procedures in greater comfort for longer periods of time without sacrificing acute visual control.

It also is within the scope and teachings of the present invention to digitally process the real-time high resolution video signal transmitted from the at least one high resolution photosensor to produce a high definition video display of the target object or tissue having a resolution of at least about 1280 lines×720 lines. Further, where the high resolution photosensor of the present invention is capable of receiving at least two optical views of the target object or tissue, it is within the scope of the present invention to present the visual signal in high definition on a three dimensional ("3D") video display. This greatly facilitates the operator's ability to perform the procedures under low ambient light conditions at an enhanced level relative to prior art systems.

The three dimensional high definition views provided by the present invention can be presented on a relatively large conveniently located screen without giving up the sense of depth and relative space needed to perform a meticulous or delicate procedure without the need for relatively high levels of ambient lighting. The 3D visualization provided by the present invention also is a huge benefit for operators and surgeons learning how to operate or honing a new technique or procedure. For example, a teaching physician can demonstrate a procedure to students in real-time 3D on a screen visible to those besides the operating surgeon.

DETAILED DESCRIPTION OF THE INVENTION

Figure 1:
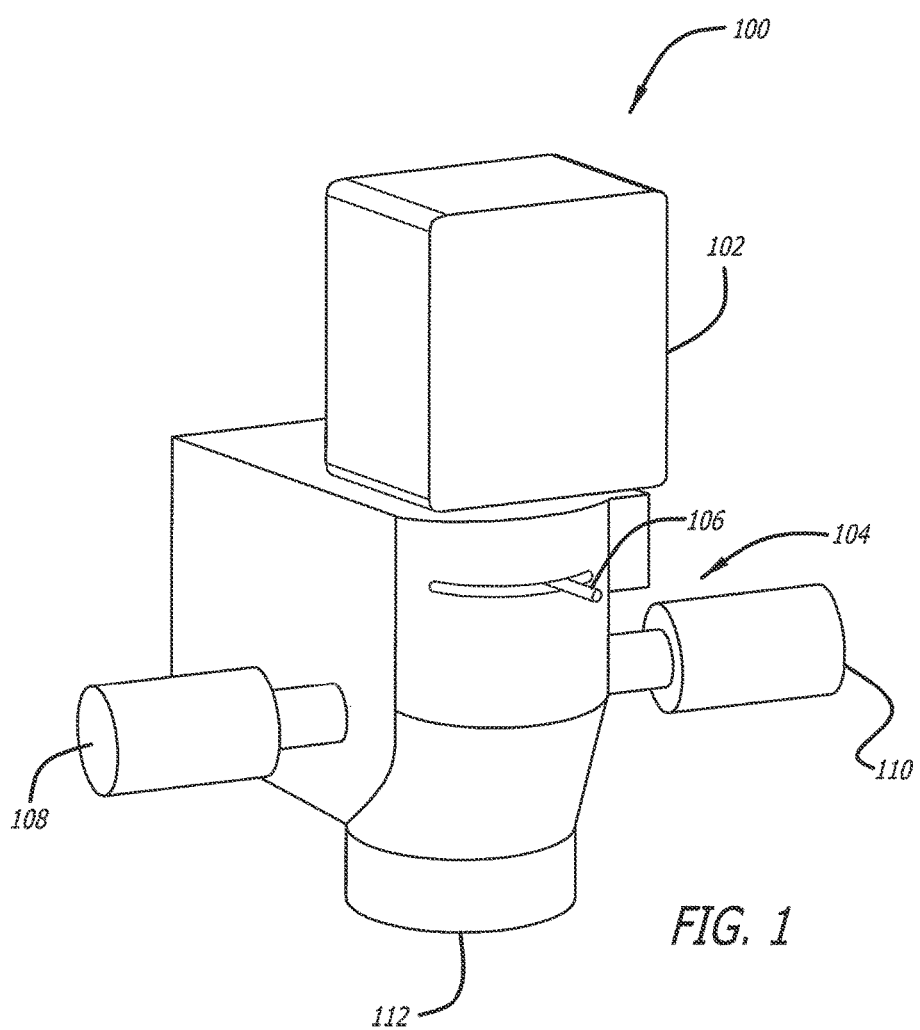
FIG. 1 is an illustration of an exemplary apparatus of the present description retrofitted on a surgical microscope.

The present disclosure generally is related to apparatus and methods for visualization. More particularly, the apparatus and methods of the present invention provide novel visualization platforms for performing enhanced visually directed procedures on target objects or tissues under low ambient lighting conditions. The visualization platforms of the present invention can be configured to function as a stand-alone apparatus or can be retro-fit to existing process control or monitoring optical systems such as stereomicroscopes used in precision manufacturing and testing as well as in microsurgical techniques.

In a broad aspect the visualization platforms of the present invention include at least one high resolution photosensor such as a camera or charge coupled device which is capable of receiving and acquiring a plurality of optical views of the target object of the process in at least one wavelength of light outside of the wavelengths of normal visible light. Those skilled in the art will appreciate that receiving light in visible wavelengths in addition to wavelengths outside of the wavelengths of normal visible light is also within the scope of the present invention. The high resolution photosensor then transmits a resultant real-time high resolution video signal which is received by at least one high resolution video display. Because of the multiple high resolution optical views transmitted and presented on the display, the operator of the visualization platform, or others, is able to view a real-time high definition three dimensional visual image of the target object or tissue provided by the present invention in spite of the absence of substantial amounts of ambient or direct visible light.

In direct contrast to the prior art where reducing visible light reduces the ability to view the process target, the real-time high definition three dimensional visual images of the present invention provide the process operator with precise views of minute visual details as well as the real-time responses of the target objects and tissues involved to the various steps of the processes. As a result, the process operator is able to manipulate and control the target object or tissues with a high degree of precision even though the presence of visible light is markedly reduced or even essentially eliminated.

As an added benefit, by reducing or significantly lowering ambient lighting in the visible wavelengths the present invention makes the operating environment for conducting the process more comfortable for the process operator by reducing the heat associated with traditional high output visible lighting. Removing the need for such lighting also frees up valuable process or operating room space that would normally be occupied by lighting fixtures, associated power cords, and the like. In addition to simplifying and to significantly improving the comfort and stamina of the process operator or surgeon, where appropriate to the target object or tissue, reducing heat in the vicinity of the target object or tissue can avoid drying, bleaching, or otherwise damaging the process target.

The inventive apparatuses described herein can be embodied in a single device which can be retrofitted onto existing surgical equipment such as surgical microscopes or open surgery apparatus. This is highly advantageous as the retrofit embodiments can be added to existing systems, allowing expensive equipment to simply be upgraded as opposed to purchasing an entirely new system. The exemplary apparatus can include various optical or electronic magnification systems including stereomicroscopes or can function as open surgery apparatus utilizing cameras and overhead visualizations with or without magnification.

An exemplary real-time multidimensional visualization module suitable for practicing the present methods incorporates the basic structural components of the Applicant's TrueVision Systems, Inc. real-time 3D HD visualization systems described in the Applicant's co-pending U.S. applications: Ser. No. 11/256,497 entitled "Stereoscopic Image Acquisition Device," filed Oct. 21, 2005; Ser. No. 11/668,400, now U.S. Pat. No. 8,339,447, entitled "Stereoscopic Electronic Microscope Workstation," filed Jan. 29, 2007; Ser. No. 11/668,420, now U.S. Pat. No. 8,358,330, entitled "Stereoscopic Electronic Microscope Workstation," filed Jan. 29, 2007; and Ser. No. 11/739,042 entitled "Stereoscopic Display Cart and System," filed Apr. 23, 2007; all of which are fully incorporated herein by reference as if part of this specification.

Turning next to the Figures, FIG. 1 illustrates the functional portion of a surgical microscope 100 retrofitted with an exemplary visualization platform of the present invention for performing an enhanced visually directed procedure on a target object or tissue under low ambient visible light and incorporating image capture module 102 which includes a multidimensional visualization module and an image processing unit, both housed within image capture module 102, and therefore, not depicted. Image capture module 102 may be associated with one or more displays, for example, monitors or overhead displays. The exemplary image capture module of the present invention includes at least one high resolution photosensor capable of acquiring a plurality of optical views to capture still images, photographs or video images of a target in at least one wavelength of light outside of the wavelengths of visible light and transmitting a resultant real-time high resolution video signal to the at least one associated high resolution video display.

As those skilled in the art will appreciate, a photosensor is an electromagnetic device that responds to light and produces or converts light energy into an electrical signal which can be transmitted to a receiver for signal processing or other operations and ultimately read by an instrument or presented to an observer on a display. Image capture module 102 is mounted, integrated, or secured to surgical microscope 104 in place of the microscope's binocular eyepiece. Although surgical microscope 104 has been retrofitted with image capture module 102, it still retains the use of conventional controls and features such as, but not limited to, iris adjustment knob 106, first adjustment knob 108, second adjustment knob 110 and objective lens 112.

Figure 2:
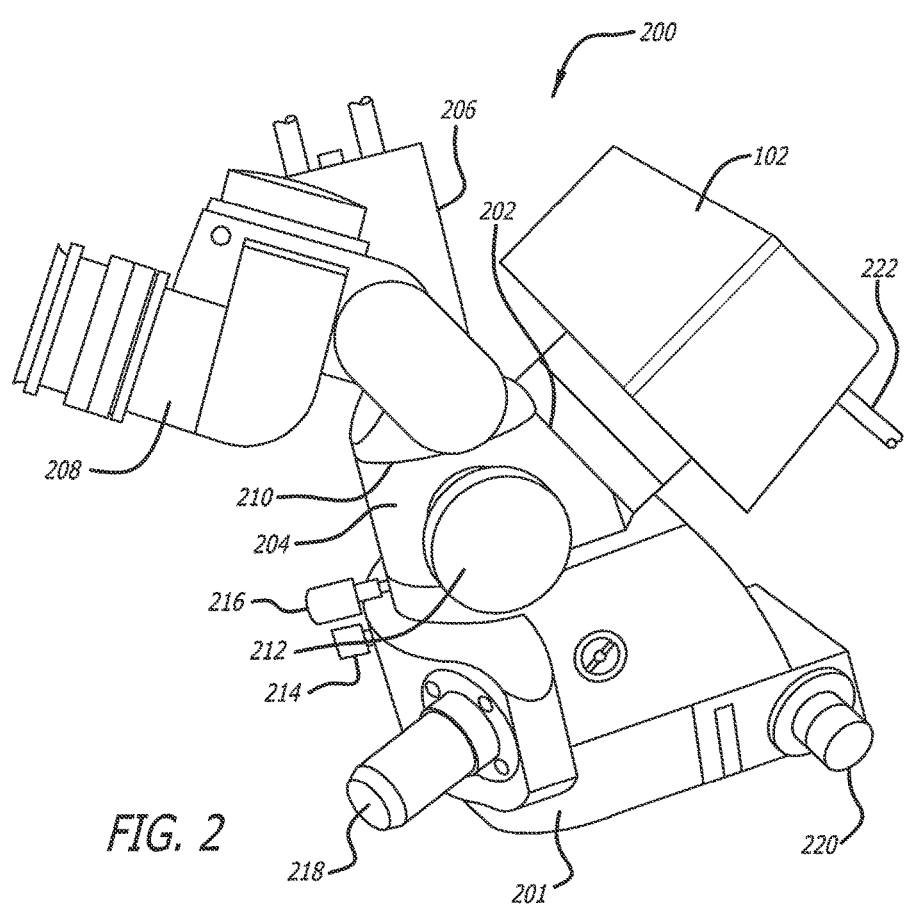
FIG. 2 is an illustration of an alternative exemplary apparatus of the present description retrofitted on a surgical microscope including an optical eyepiece.

Turning next to FIG. 2, an alternative embodiment of the visualization platform of the present invention is shown with image capture module 102 retrofitted onto second surgical microscope 201. Within this alternative embodiment of the present invention image capture module 102 is coupled to first ocular port 202 on ocular bridge 204 of second surgical microscope 201. Further illustrating the adaptability of the present invention to multiple configurations of microscopes and ancillary equipment, ocular bridge 204 also couples video camera 206 to a second ocular port on the rear of microscope 201 and therefore not visible in FIG. 2 as well as binocular eyepiece 208 to third ocular port 210. An optional fourth ocular port 212 is available for coupling additional eyepieces and cameras to surgical microscope 201 where desired. Thus, although surgical microscope 201 has been updated or even retrofitted with image capture module 102, it retains the use of conventional controls and features such as, but not limited to, iris adjustment knob 214, first adjustment knob 216, second adjustment knob 218, illumination control knob 220 and can be operated in a manner that is familiar to those of ordinary skill in the art.

Also shown in FIG. 2 is signal cable 222. In accordance with the teachings of the present invention, image capture module 102 can send and receive information such as real-time high resolution video signals or control inputs through signal cable 222 to a variety of additional components including at least one high resolution video display or one or more recording devices. Those skilled in the art will appreciate that signal cable 222 is exemplary only and that alternative means for transmitting real-time high resolution video signals or control inputs to and from image capture module 102 such as wireless transmitters are within the scope of the present invention.

Figure 3:
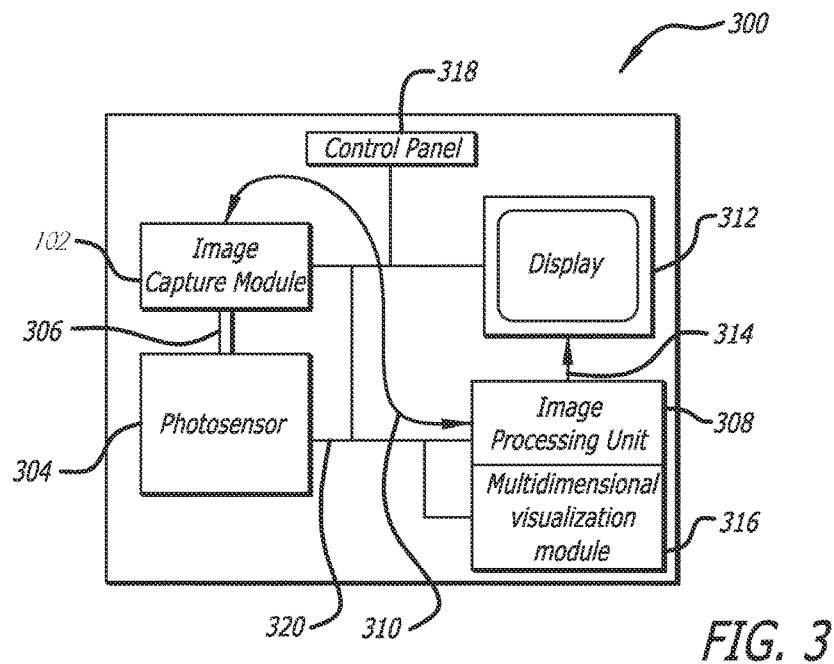
FIG. 3 is a schematic overview of an exemplary embodiment of an apparatus of the present description illustrating features thereof.

A further understanding of the low ambient visible light visualization platform of the present invention is provided by the exemplary, non-limiting configuration of visualization platform components illustrated in FIG. 3. Visualization platform 300 includes image capture module 102, coupled to photosensor 304 by bi-directional link 306. Those skilled in the art will appreciate that bi-directional link 306 can be eliminated where image capture module 102 and photosensor 304 are physically the same device. Image capture module 102 is in direct communication with image processing unit 308 by first cable 310. First cable 310 can be a cable connecting to physically different devices or a cable connecting two physically different components within the same device, or can be eliminated if image capture module 102 and image processing unit 308 are physically the same device.

First cable 310 allows, in certain embodiments of the present invention, bi-directional communication between image capture module 102 and image processing unit 308. Image processing unit 308 generates images and videos that are visually presented to an observer on display 312. It is within the scope of the present description that display 312 include multiple displays or display systems (e.g. projection displays). An electrical signal (e.g. video signal) is transmitted from image processing unit 308 to display 312 by a second cable 314, which is any kind of electrical signal cable commonly known in the art. Image processing unit 308 can be in direct communication with multidimensional visualization module 316, which can also send electrical signals to display 312 via second cable 314. In one embodiment, image capture module 102, image processing unit 308, and multidimensional visualization module 316 are all housed in a single device or are physically one single device. Further, one or all of the components of the present invention can be manipulated by control panel 318 via cable network 320. In alternative embodiments, control panel 318 is wireless and uses radio signals to transmit control data or optical using fiber optics and light to transmit control data.

"Display," as used herein, can refer to any device capable of displaying a still or video image. Preferably, the displays of the present disclosure display high definition (HD) still images and video images or videos which provide a surgeon with a greater level of detail than a standard definition (SD) signal. More preferably, the displays present such HD stills and images in three dimensions (3D). Exemplary displays include HD monitors, cathode ray tubes, projection screens, liquid crystal displays, organic light emitting diode displays, plasma display panels, light emitting diodes, 3D equivalents thereof and the like. 3D HD holographic display systems are considered to be within the scope of the present disclosure. In one embodiment, display 312 is a projection cart display system and incorporates the basic structural components of the Applicant's TrueVision Systems, Inc. stereoscopic image display cart described in the Applicant's co-pending U.S. application: Ser. No. 11/739,042, entitled "Stereoscopic Display Cart and System" filed Apr. 23, 2007, which is fully incorporated herein by reference as if part of this specification.

The exemplary image processing units as illustrated in FIGS. 1, 2 and 3 include a microprocessor or computer configured to process data sent as electrical signals from image capture module 102 and to send the resulting processed information to display 312, which can include one or more visual displays for observation by a physician, surgeon or a surgical team. Image processing unit 308 may include control panel 318 having user operated controls that allow a surgeon to adjust the characteristics of the data from image capture module 102 such as the color, luminosity, contrast, brightness, or the like sent to the display.

In one embodiment, image capture module 102 includes a photosensor, such as a camera, capable of capturing a still image or video images, preferably in 3D and HD. It is within the teachings of the present invention that the photosensor is capable of responding to any or all of the wavelengths of light that form the electromagnetic spectrum. Alternatively, the photosensor may be sensitive to a more restricted range of wavelengths including at least one wavelength of light outside of the wavelengths of visible light. "Visible light," as used herein, refers to light having wavelengths corresponding to the visible spectrum, which is that portion of the electromagnetic spectrum where the light has a wavelength ranging from about 380 nanometers (nm) to about 750 nm.

More specifically, the one or more data processors are also in direct communication with multidimensional visualization module 316 and/or image capture module 102. In one embodiment, the data processor or processors are incorporated into multidimensional visualization module 316. In another embodiment, at least one data processor is a stand alone processor such as a workstation, personal data assistant or the like.

The exemplary one or more data processors are controlled by built-in firmware upgradeable software and at least one user control input, which is in direct communication with the data processors. The at least one user control input can be in the form of a keyboard, mouse, joystick, touch screen device, remote control, voice activated device, voice command device, or the like.

Figure 4:
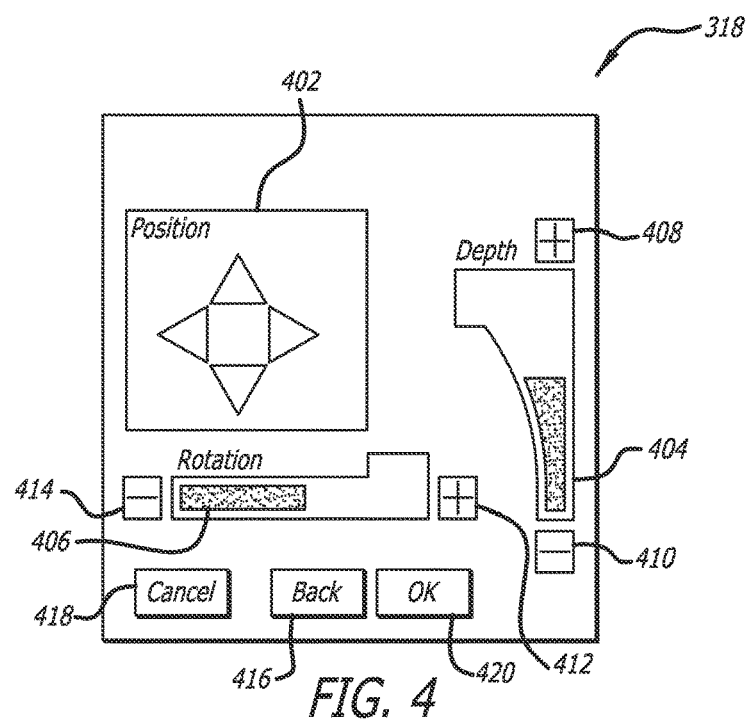
FIG. 4, is a plan view of an exemplary alignment control panel of the present description illustrating an exemplary embodiment of a user input control thereof.

FIG. 4 illustrates such an exemplary user control input, in the form of control panel 318. Control panel 318 includes multidirectional navigation pad 402 with user inputs allowing a controlling surgeon or operator to move data vertically, horizontally or any combination of the two. Additionally, the depth of the data can be adjusted using depth rocker 404 of control panel 318 and the rotation can be adjusted using rotation rocker 406 of control panel 318. Depth can be adjusted using both increase depth position 408 and decrease depth position 410 of depth rocker 404. Additionally, rotation can be adjusted using both increase rotation position 412 and decrease rotation position 414 of rotation rocker 406. Other non-limiting adjustments that can be made to the pre-operative image or to the real-time visualization include changes in diameter, opacity, color, horizontal and vertical size, and the like, as known in the art. It should be noted that in exemplary control panel 318 an adjustment can be undone by the surgeon utilizing "back" button 416. Further, the entire process can be ended by the surgeon by engaging "cancel" button 418. Further, once the surgeon is satisfied with the alignment of the data, the alignment is locked into place by engaging "ok" button 420.

Alternative control panel embodiments for the manipulation and alignment of the pre-operative still image are contemplated as being within the scope and teachings of the present description. For example, a hand-held device such as a 3D mouse can be used as known in the art to directly position templates, images, and references within the real-time multidimensional visualization. Such devices can be placed on a tabletop or held in mid-air while operating. In another embodiment, foot switches or levers are used for these and similar purposes. Such alternative control devices allow a surgeon to manipulate the pre-operative still image without taking his or her eyes off of the visualization of a surgical procedure, enhancing performance and safety.

In yet another alternative embodiment of the present invention, a voice activated control system is used in place of, or in conjunction with, control panel 318. Voice activation allows a surgeon to control the modification and alignment of the pre-operative still image as if he was talking to an assistant or a member of the surgical team. As those skilled in the art will appreciate, voice activated controls typically require a microphone and, optionally, a second data processor or software to interpret the oral voice commands. In yet a further alternative embodiment, the apparatus utilizes gesture commands to control pre-operative image adjustments. Typically, as known in the art, the use of gesture commands involves an apparatus (not shown) having a camera to monitor and track the gestures of the controlling physician and, optionally, a second data processor or software to interpret the commands.

Visualization platform 300 can be used in a wide variety of medical and non-medical settings. For example, visualization platform 300 can be used in a medical examination room. In such an environment, image capture module 102 utilizes photosensor 304 to capture pre-operative patient data such as still images, preferably in HD. Photosensor 304 can be coupled to any piece of medical equipment that is used in an examination room setting wherein pre-operative data can be captured. Image capture module 102 directs this data to image processing unit 308. Image processing unit 308 processes the data received from image capture module 102 and presents it on display 312.

Alternatively, visualization platform 300 can be used in an operating room. There image capture module 102 utilizes photosensor 304 to capture a real-time visualization of at least a portion of the target surgical field, preferably in HD, and more preferably in HD 3D. Image capture module 102 directs this data to image processing unit 308 including multidimensional visualization module 316. Image processing unit 308 including multidimensional visualization module 316 processes the data received from image capture module 102 and presents it on display 312 in real-time.

In one exemplary embodiment, visualization module 300 is used in an operating room and photosensor 304 is a surgical microscope. For example, image capture module 102 can be retrofitted to an existing surgical microscope or provided as a unitary component of a new microscope. The use of a surgical microscope in combination with visualization platform 300 allows a surgeon to comfortably visualize a surgical procedure on one or more displays instead of staring for hours, in many cases, though the eyepiece of a surgical microscope for the extent of a surgical procedure.

Visualization module 300 used in an examination room can be in direct communication with a corresponding visualization platform 300 used in the operating room. The two apparatus can be directly connected either wirelessly or by cable, or indirectly connected through an intermediary device such as a computer server. In some embodiments, the two sections can be separate systems, even in different physical locations. Data can be transferred between the two systems by any means known to those skilled in the art such as an optical disc, a flash memory device, a solid state disk drive, a wired network connection, a wireless network connection or the like.

In medical or surgical processes the reduction of visible ambient lighting and the associated heat and complexity in the operating room also adds to the comfort of a surgical patient and enhances the compliance of the patient with the needs of the surgeon. As a result, the present invention can simplify and shorten the medical procedure and improve its outcome; all while providing the surgeon with enhanced visual control of the process.

Further enhancing the operator's or surgeon's visual control of the process, by reducing ambient visible lighting the present invention functions to reduce reflected glare and high contrast shadows in the process environment that can confuse or overwhelm the vision of the operator or surgeon. In the past, the operator or surgeon would have to reposition equipment or personnel relative to the lighting source to prevent shadows, possibly compromising his vision of the process target or his ability to perform a process step. Similarly, when the operator or surgeon would have to shift his focus away from the target object and back again in order to adjust equipment or to change tools the changes in ambient lighting would require that he pause in order to allow his own eyes to adjust to the changes in lighting. The present invention eliminates these pauses and delays by reducing the visible contrast in ambient lighting while it facilitates the operator's or surgeon's ability to view the surrounding environment under relatively consistent and comfortable lighting levels while maintaining accurate visual control of the target process.

This is accomplished by the exemplary embodiments of the present invention which provide a visualization platform for performing an enhanced visually directed procedure on a target object or tissue under low ambient visible light is provided. The visualization platform includes at least one high resolution photosensor capable of acquiring a plurality of optical views of the target object in at least one wavelength outside of the wavelengths of visible light.

"Visible light" as used herein refers to light having wavelengths corresponding to the visible or optical spectrum. It is that portion of the electromagnetic spectrum where the light has a wavelength ranging from about 380 nanometers to about 750 nanometers (nm). The familiar colors of the rainbow include all of the colors that make up visible or white light; whereas a single wavelength produces a pure monochromatic color. For example, the color blue corresponds to wavelengths of 450-495 nm and the color yellow corresponds to wavelengths of 570-590 nm. A typical human eye will respond to wavelengths in air from about 380 nanometers to about 750 nanometers. In terms of frequency, these wavelengths correspond to a spectral band ranging from about 400-790 terahertz (THz). A light-adapted human eye generally has its maximum sensitivity at around 555 nm (corresponding to a frequency of 540 THz), in the green region at the mid-range of the optical spectrum.

The exemplary visualization platform of the present invention includes at least one high resolution photosensor which can detect at least one wavelength outside of this range. As those skilled in the art will appreciate, wavelengths of light outside of the wavelengths of normal visible light can be shorter than or longer than the wavelengths of visible light. Exemplary wavelengths that are outside of the wavelengths of normal visible light within the scope of the present invention include at least one longer wavelength that is between about 700 nm and about 1400 nm. Exemplary wavelengths that are outside of the wavelengths of normal visible light within the scope of the present invention also include wavelengths of light that are shorter than the wavelengths of visible light. These include wavelengths in the ultraviolet range or "UV" range from about 400 nm or less.

More specifically, exemplary longer wavelengths can include wavelengths between about 700 nm to about 1000 nm or 1 micrometer. As those skilled in the art also will appreciate, such longer than visible wavelengths are commonly referred to as infrared or "IR" wavelengths and are not visible to the eye. Infrared radiation is electromagnetic radiation typically of a wavelength longer than that of visible light, but shorter than that of microwaves. There are different regions in the infrared portion of the electromagnetic spectrum. Near-infrared corresponds to light with a wavelength between about 700 nm to about 1400 nm. Short infrared corresponds to light with a wavelength between about 1.4 micrometers (μm) to about 3 μm. Mid-wavelength infrared corresponds to light with a wavelength between about 3 μm to about 8 μm. Long-wavelength infrared corresponds to light with a wavelength between about 8 μm to about 15 μm. Far infrared corresponds to light with a wavelength between about 15 μm to about 1 mm.

The exemplary visualization platform of the present invention includes at least one high resolution photosensor. A photosensor is an electromagnetic sensor that responds to light and produces or converts it to an electrical signal which can be transmitted to a receiver for signal processing or other operations and ultimately read by an instrument or an observer. It may be capable of responding to or detecting any or all of the wavelengths of light that form the electromagnetic spectrum. Alternatively, the photosensor may be sensitive to a more restricted range of wavelengths including the at least one wavelength of light outside of the wavelengths of visible light.

One broad example of a photosensor which the present visualization platforms can include is a camera. A camera is a device used to capture images, either as still photographs or as sequences of moving images (movies or videos). A camera generally consists of an enclosed hollow with an opening (aperture) at one end for light to enter, and a recording or viewing surface for capturing the light at the other end. The recording surface can be chemical, as with film, or electronic. Cameras can have a lens positioned in front of the camera's opening to gather the incoming light and focus all or part of the image on the recording surface. The diameter of the aperture is often controlled by a diaphragm mechanism, but alternatively, where appropriate, cameras have a fixed-size aperture. Either configuration is contemplated as being within the scope of the present invention.

Exemplary electronic photosensors in accordance with the teachings of the present invention include, but are not limited to, complementary metal-oxide-semiconductor (CMOS) sensors or charge-coupled device (CCD) sensors. Both types of sensors perform the function of capturing light and converting it into electrical signals. A CCD is an analog device. When light strikes the CCD it is held as a small electrical charge. The charges are converted to voltage one pixel at a time as they are read from the CCD. A CMOS chip is a type of active pixel sensor made using the CMOS semiconductor process. Electronic circuitry generally located next to each photosensor converts the received light energy into an electrical voltage and additional circuitry then converts the voltage to digital data which can be transmitted or recorded.

The real-time high resolution video signal transmitted in the present invention can be a digital video signal which is a digital representation of discrete-time signals. Often times, digital signals are derived from analog signals. By way of background, an analog signal is a datum that changes over time, such as the temperature at a given location or the amplitude of the voltage at some node in a circuit. It can be represented as a mathematical function, with time as the free variable (abscissa) and the signal itself as the dependent variable (ordinate). A discrete-time signal is a sampled version of an analog signal where the value of the datum is noted at fixed intervals (for example, every microsecond) rather than noted continuously. Where the individual time values of the discrete-time signal, instead of being measured precisely (which would require an infinite number of digits), are approximated to a certain precision—which, therefore, only requires a specific number of digits—then the resultant data stream is termed a "digital" signal. The process of approximating the precise value within a fixed number of digits, or bits, is called quantization. Thus, a digital signal is a quantized discrete-time signal, which in turn is a sampled analog signal. Digital signals can be represented as binary numbers, so their precision of quantization is measured in bits.

With this understanding it will be appreciated by those of ordinary skill in the art that by attaching the exemplary photosensor of the present invention to a visualization device such as a stereomicroscope which directs a plurality of views of a target object onto the photosensor the present invention is able to acquire a plurality of optical views of a target object. Alternatively, it is contemplated as being within the scope of the present invention to utilize multiple photosensors, each receiving light corresponding to a different view of a target object and transmitting that information as a real-time high resolution video signal that can be recorded or presented for display and viewing. In an exemplary embodiment of the present invention, the transmitted digital video signal is capable of producing an image having a resolution of at least about 1280 lines by 720 lines. This resolution corresponds to the typically minimum resolution for what one of ordinary skill in the art would consider to be high definition or an HD signal.

The signals transmitted from the at least one photosensor are real-time high resolution video signals. "Real-time" as used herein generally refers to the updating of information at the same rate as data is received. More specifically, in the context of the present invention "real-time" means that the image data is acquired, processed, and transmitted from the photosensor at a high enough data rate and a low enough delay that when the data is displayed objects move smoothly without user-noticeable judder or latency. Typically, this occurs when new images are acquired, processed, and transmitted at a rate of at least about 30 frames per second (fps) and displayed at about 60 fps and when the combined processing of the video signal has no more than about $\frac{1}{30}^{th}$ second of delay.

The transmitted video signal of the present invention resulting from focusing the visible or non-visible wavelengths of light onto the at least one high resolution photosensor is a "high-resolution" video signal having a resolution of at least 1024 lines by 728 lines. It is also contemplated as being within the scope of the present invention for the video signal to be a "high definition" signal. High-definition (HD) generally refers to a video signal having a higher resolution than a standard-definition (SD) video signal, most commonly at display resolutions of 1280 by 720 lines (720 p) or 1920 by 1080 lines (1080 i or 1080 p).

When the high resolution video signal is received and presented on a video display having corresponding high resolution or HD capabilities the resultant image provides a degree of clarity, detail, and control previously unattainable in the absence of high ambient visual light. Exemplary visual displays within the scope and teachings of the present invention include, without limitation, cathode ray tubes, projection screens, liquid crystal displays, organic light emitting diode displays, plasma display panels and light emitting diode displays.

Moreover, when the real-time high resolution video signal of the present invention includes multiple views of the target object or tissue the video display can be made three dimensional ("3D") so that depth of field is presented to the process operator by presenting a different image of the target object or tissue to each eye in spite of the relative absence of ambient visible light. It is contemplated as being within the scope and teachings of the present invention to utilize many types of high resolution 3D video displays including, without limitation, stereoscopic 3D displays using polarized glasses much like the visualization systems provided by the present inventors and marketed under the name TrueVision Systems, Inc., which are the subject of co-pending U.S. patent applications Ser. Nos. 11/256,497 filed Oct. 21, 2005, Ser. No. 11/739,042 filed Apr. 23, 2007, Ser. No. 11/668,400 filed Jan. 29, 2007, and Ser. No. 11/668,420 filed Jan. 29, 2007. Alternatively, autostereoscopic 3D displays that do not require the use of any special glasses or other head gear to direct different images to each eye can be used. Similarly, holographic 3D displays are also contemplated as being within the scope of the present invention and reproduce a light field which is substantially identical to that which emanated from the original target.

In a broader aspect, target objects and tissues which are contemplated for use in conjunction with the present invention include anything for which visualization with wavelengths of light outside of wavelengths of visible light would be beneficial. These include, without limitation, microelectronics and micromechanical articles and devices or other precision devices such as watches, jewelry, and the like. They also may include, without limitation, tissues within the human body such as the eyes, ears, nose, and throat, the brain, heart, nerves, vasculature, joints, tumors, or any other part of the human body.

A further understanding of the features and benefits of the visualization platforms and associated methods of the present invention will be provided to those of ordinary skill in the art in the following non-limiting context of an exemplary medical procedure where the target object or tissue is the human eye or part of the human eye and the enhanced visually directed procedure is laser surgery. As used herein, laser surgery generally refers to any surgical procedure which uses a laser. For example, laser surgery may refer to the use of a laser scalpel to cut or remove tissue.

In ophthalmology a particular type of laser known as an excimer laser is used to change the shape of the cornea in procedures known as LASIK and LASEK, which is an acronym for "Laser Assisted In Situ Keratomileusis" (LASIK) and "Laser Assisted Sub-Epithelial Keratectomy" (LASEK). These procedures are intended to correct a patient's vision by reshaping the cornea to compensate for refractive errors and aberrations, thereby reducing the patient's dependency on glasses or contact lenses. LASEK permanently changes the shape of the anterior central cornea using an excimer laser to ablate (remove by vaporization) a small amount of tissue from the corneal stroma at the front of the eye, just under the corneal epithelium. The outer layer of the cornea is removed prior to the ablation. LASEK is distinct from LASIK which is a form of laser eye surgery where a permanent flap is created in the deeper layers of the cornea prior to vaporization and resculpting the contours of the cornea.

Though the present invention is equally applicable to either type of surgery, for purposes of explanation and not of limitation the exemplary embodiments will be discussed in the context of LASIK surgery. LASIK is fast becoming a common procedure performed by ophthalmologists for correcting myopia, hyperopia, and astigmatism. The first step in the LASIK procedure is to immobilize the target eye of the patient so that a flap of corneal tissue can be created to preserve the delicate outer layer of the cornea while exposing the underlying layers. Typically, a corneal suction ring is applied to the eye, holding the eye in place. Once the eye is immobilized, a flap is created either with a mechanical microkeratome slicing a thin layer of the outer cornea using a metal blade, or with a femtosecond laser microkeratome that creates a series of tiny closely spaced bubbles within the cornea underneath the outer corneal layer. With either flap forming technique a hinge of uncut tissue is left at one end of the flap. In either technique, great care must be taken to avoid damaging the outer layer of the cornea and the procedure is typically carried out under bright ambient lighting so that the surgeon can control the process.

Next, the flap is folded back to expose the middle layers of the cornea known as the stroma. Then a pulsed excimer laser is used to remodel the corneal stroma by vaporizing corneal tissue in a finely controlled manner without damaging adjacent tissue because the laser is precisely controlled and no heat or burning is required to ablate the tissue. The layers of stromal tissue removed are extremely thin, only tens of micrometers thick. After the stromal layer has been resculpted or reshaped with the laser the flap is carefully folded back and repositioned over the treatment area by the surgeon and checked to verify the absence of air bubbles or debris and to verify a proper fit on the eye. No sutures are needed to fix the flap in place as it remains in position by natural adhesion until healing is completed.

The amount of stromal tissue ablated and the contour of corneal resculpting is determined by measuring the unaided eye's ability to refract light prior to the procedure. At present, the most accurate method for doing so is to determine a "waveform" representing how light passes through the interior volume of the eye. This non-invasive procedure identifies focusing errors and other abnormalities that the LASIK procedure can correct by removing different amounts of stromal tissue at varying locations about the optical axis of the cornea. Ideally, waveform measurements are made in a darkened room so that the patient's pupil will dilate and thereby allow a greater area of the cornea to be exposed for ocular measurement. For example, a pupil that is constricted under bright visible light may only allow measurement relative to a circular area of the cornea approximately 1.5 mm in diameter whereas a dilated pupil may allow measurement of a circular area closer to 8 to 10 mm in diameter.

However, prior to the present invention having a more complete and accurate waveform was of little use because the LASIK procedure itself was performed under bright visible lighting which caused the patient's pupil to constrict. Because pupils are not perfectly centered and may constrict asymmetrically this made it difficult for the LASIK surgeon to align the LASIK apparatus with a pupil that no longer resembled the pupil of the waveform measurement. As a result, an annular ring of corneal surface outside of the diameter of the constricted pupil was difficult to recontour effectively. The resultant LASIK procedure was still effective at correcting the patient's vision, but at night or in dark environments where the patient's pupil would dilate the patient might experience less than ideal vision as light passed through newly exposed areas of the cornea that were not able to be resculpted due to the pupillary constriction experienced under the bright lighting conditions of traditional LASIK procedures.

Utilizing the teachings of the present invention a LASIK surgeon is able to overcome these drawbacks and to more completely resculpt the cornea in response to the entire ocular waveform measurement in order to achieve enhanced visual improvements and improved night vision as well. This is accomplished by first inspecting the eye of the patient under light conditions having visible light present in amounts that are insufficient to cause the pupil of the patient's eye to constrict substantially from its maximum pupillary diameter; in other words, in a darkened room. Then, the LASIK procedure is performed under light conditions that are substantially identical to the light conditions of this inspecting step so that the patient's pupil will dilate to essentially the same extent as it was during the inspecting and measuring step when the waveform was determined.

Performing the corneal resculpting in a darkened environment allows the LASIK surgeon to operate on an eye having familiar dimensions and appearance which facilitates his ability to align the LASIK apparatus and to more aggressively contour the outer corneal areas located more distant from the optical axis of the patient's eye. Without the benefit of the present invention performing such an enhanced visually directed procedure under low ambient visible light conditions would be essentially impossible because the surgeon would be unable to see and control what was going on with the process. However, utilizing the teachings of the present invention the surgeon is able to "dial down" the ambient visible lighting without sacrificing precise visual control because the present invention utilizes one or more wavelengths of light that are outside of the wavelengths of normal visible light to transmit a resultant real-time high resolution video signal to a conveniently positioned high resolution 3D visual display presenting the details of the process to the surgeon in exquisite detail with a realistic depth of field.

Moreover, the present invention makes the process more comfortable for both the surgeon and the patient by substantially eliminating harsh bright lighting and the associated heat and complexity in the process environment. As a result, the LASIK operator is better able to use his own vision without having to pause or adjust to differing levels of brightness which both simplifies and expedites the process without sacrificing quality or control. Similarly, under the low ambient visible light conditions of the present invention the more comfortable patient is less likely to move or twitch as might happen in response to the bright visible lighting of conventional processes, further improving the performance of the procedure and enhancing its outcome.

As those skilled in the art will appreciate, these benefits and advantages of the present invention are equally applicable to a wide variety of processes and procedures beyond LASIK. For example, many ocular procedures involve accessing tissues within the ocular volume such as the retina or ocular lens capsules. Because the present invention provides apparatus and methods for conducting these procedures under low ambient light conditions it provides enhanced access to such tissues within the eye by dilating the patient's pupil to a near maximum extent without sacrificing visual control of the process or without sacrificing open pupillary access to internal eye tissues in exchange for illuminating those tissues with sufficient light to make them visible to operate on.

Accordingly, the present invention is useful in a wide variety of medical and surgical procedures where both doctor comfort and patient comfort are important and where enhanced control is beneficial. Exemplary procedures include, without limitation, treatment of tissues within the human body such as the eyes, ears, nose, and throat, the brain, heart, vasculature, joints, tumors, or any other part of the human body.

Similarly, the present invention has direct applicability outside of the medical profession. For example, precision manufacturing or inspection processes requiring precise degrees of control and visualization also benefit from the improved comfort the present invention provides to the process environment in conjunction with the enhanced visual acuity and control of the inventive methods and apparatus. Microelectronic technicians and the like can work longer periods of time with improved levels of concentration and performance when they are provided with the enhanced visual capacities of the present invention in conjunction with a more comfortable working environment that is free from excessive heat, glare, and shadows.

Prior to the present invention, most doctors and precision technicians utilized stereomicroscopes to view their target objects, tissues, and work pieces. This required them to look through the binocular eyepieces of their microscopes for hours on end. The present invention visualization platforms and associated methods take the place of the microscope eyepieces either directly or as a retro-fit and feed real-time high definition digital video data to 3D displays or projectors which can be conveniently mounted on a workstation or a cart. Unlike microscopes, because the display can be viewed by more than one person at a time, the present invention is very useful for teaching.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention is claimed as follows:

1. A method for performing an enhanced visually directed procedure under low ambient visible light on a patient's eye, the method comprising:
   instructing, via the processor, or causing an intensity of ambient visible light for imaging the patient's eye to be low enough such that a pupil of the eye does not constrict substantially from its maximum pupillary diameter,
   acquiring, from at least one high resolution photosensor, at least one first real-time high resolution video signal representing at least one view of the eye in at least one wavelength of light outside of the wavelengths of visible light;
   acquiring, from the at least one high resolution photosensor or a different high resolution photosensor, at least one second real-time high resolution video signal representing the at least one view of the eye in visible light;
   converting, via a processor, the at least one view corresponding to the at least one first real-time high resolution video signal at the at least one wavelength of light outside of the wavelengths of visible light into at least one wavelength of visible light;
   combining, via the processor, the at least one wavelength of visible light with the visible light of the least one second real-time high resolution video signal to form at least one third real-time high resolution video signal; and
   displaying, via the processor, the at least one view corresponding to the at least one third real-time high resolution video signal including the at least one wavelength of visible light, wherein the display of the at least one third real-time high resolution video signal is brighter than a display of the at least one second real-time high resolution video signal and enables the intensity of the ambient visible light to be low enough such that a pupil of the eye does not constrict substantially from its maximum pupillary diameter.

2. The method of claim 1, further comprising:
   inspecting the eye of the patient; and
   performing an ocular procedure on the eye.

3. The method of claim 2, wherein the procedure is laser surgery.

4. The method of claim 2, wherein the procedure is laser assisted in situ keratomileusis.

5. The method of claim 2, wherein inspecting includes determining a waveform for the eye.

6. The method of claim 1, wherein the ambient visible light includes light having a wavelength of about 700 nanometers to about 1400 nanometers.

7. The method of claim 1, wherein the ambient visible light includes light having a wavelength of about 700 nanometers to about 1 micrometer.

8. The method of claim 1, wherein the at least one third real-time high resolution video signal is displayed in high definition.

9. The method of claim 1, wherein the at least one third real-time high resolution video signal represents at least two views of the eye, and wherein the views are presented in high definition on a three dimensional video display.

10. A method for enhancing control of a visually directed eye procedure on a patient's eye having a pupil under low ambient visible light, the method comprising:
    instructing, via a processor, or causing an intensity of ambient visible light for imaging the patient's eye to be low enough such that the pupil of the eye does not constrict substantially from its maximum pupillary diameter;
    acquiring, from at least one high resolution photosensor, at least one first real-time high resolution video signal representing at least one view of the eye in at least one wavelength of light outside of the wavelengths of visible light;
    acquiring, from the at least one high resolution photosensor or a different high resolution photosensor, at least one second real-time high resolution video signal representing the at least one view of the eye in visible light;
    converting, via a processor, at least one view of the eye in the at least one wavelength of light outside of the wavelengths of visible light into at least one wavelength of visible light;
    combining, via the processor, the at least one wavelength of visible light with the visible light of the least one second real-time high resolution video signal to form at least one third real-time high resolution video signal;
    displaying the at least one view corresponding to the at least one third real-time high resolution video signal in the at least one wavelength of visible light, wherein the display of the at least one third real-time high resolution video signal is brighter than a display of the at least one second real-time high resolution video signal;
    enabling an inspection the eye of the patient under light conditions such that the intensity of the ambient visible light is insufficient to cause the pupil of the eye to constrict substantially from its maximum pupillary diameter; and
    enabling a performance of an ocular procedure on the eye under light conditions substantially identical to the light conditions for inspecting the eye.

11. The method of claim 10, wherein the intensity of the ambient visible light is selected to reduce or remove at least one of phototoxicity or dyschromatopsia in the patient.

12. The method of claim 10, wherein the intensity of the ambient visible light is selected to reduce at least one of glare or high contrast shadows related to illuminating or imaging the patient's eye.

13. The method of claim 10, wherein the at least one high resolution photosensor includes a camera or a stereoscopic image acquisition device.

14. The method of claim 10, further comprising preventing visible light from a display from illuminating the patient's eye.

15. The method of claim 10, wherein the ambient visible light includes light having a wavelength of about 700 nanometers to about 1400 nanometers or light having a wavelength of about 700 nanometers to about 1 micrometer.

16. The method of claim 10, wherein the at least one third real-time high resolution video signal is displayed at least one of stereoscopically or in high definition.

17. The method of claim 10, wherein the at least one third real-time high resolution video signal represents at least two views of the eye, and wherein the views are presented in high definition on a three dimensional video display.

18. The method of claim 10, wherein the ocular procedure includes a laser-assisted in situ keratomileusis ("LASIK") procedure.

19. The method of claim 1, wherein the intensity of the ambient visible light is essentially eliminated.

20. The method of claim 1, wherein causing the intensity of ambient visible light for imaging the patient's eye to be low enough includes prompting a surgeon, via a video screen, to lower the intensity of ambient visible light.

* * * * *